(12) United States Patent
Kirchhofer et al.

(10) Patent No.: US 6,280,421 B1
(45) Date of Patent: Aug. 28, 2001

(54) AUTOMATIC INJECTION DEVICE

(75) Inventors: Fritz Kirchhofer, Sumiswald; Jürg Steck, Kirchberg; Peter Hostettler, Ersigen; Stephan Jost, Bolligen, all of (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/311,435

(22) Filed: May 14, 1999

(30) Foreign Application Priority Data

May 15, 1998 (DE) .............................. 198 22 031

(51) Int. Cl.$^7$ .................................................. A61M 5/315
(52) U.S. Cl. ........................... 604/218; 604/207; 604/187
(58) Field of Search .................................... 604/131–135, 604/181, 187, 208–211, 218, 232, 207

(56) References Cited

U.S. PATENT DOCUMENTS

| | | |
|---|---|---|
| 4,592,745 | 6/1986 | Rex et al. . |
| 4,865,591 | 9/1989 | Sams . |
| 4,883,472 | 11/1989 | Michel . |
| 4,946,446 | 8/1990 | Vadher . |
| 4,973,318 | 11/1990 | Holm et al. . |
| 5,017,190 | 5/1991 | Simon et al. . |
| 5,084,060 | 1/1992 | Freund et al. . |

(List continued on next page.)

FOREIGN PATENT DOCUMENTS

| | | |
|---|---|---|
| 3645245 | 11/1986 | (DE) . |
| C3638984 | 11/1986 | (DE) . |
| 3900926 | 8/1989 | (DE) . |
| 4223958 | 7/1992 | (DE) . |
| 0037696 | 3/1981 | (EP) . |
| 0058536 | 8/1982 | (EP) . |
| 0245312 | 10/1986 | (EP) . |
| 0268191 | 11/1987 | (EP) . |
| 0298067 | 6/1988 | (EP) . |
| B 327910 | 1/1989 | (EP) . |
| 0373321 | 6/1990 | (EP) . |
| 496141 | 1/1991 | (EP) . |
| 0498737 | 8/1992 | (EP) . |
| 0554995 | 8/1993 | (EP) . |
| 0594349 | 4/1994 | (EP) . |
| 0627229 | 5/1994 | (EP) . |
| 2701211 | 8/1994 | (FR) . |
| WO 8702895 | 5/1987 | (WO) . |
| WO 9110460 | 7/1991 | (WO) . |
| WO 9305835 | 8/1992 | (WO) . |
| WO 9218179 | 10/1992 | (WO) . |
| WO 9316740 | 9/1993 | (WO) . |
| WO 9409841 | 5/1994 | (WO) . |
| WO 9415210 | 7/1994 | (WO) . |
| WO 9501812 | 1/1995 | (WO) . |
| WO 9504563 | 2/1995 | (WO) . |
| WO 9607443 | 3/1996 | (WO) . |

*Primary Examiner*—Richard K. Seidel
*Assistant Examiner*—Kevin C. Sirmons
(74) *Attorney, Agent, or Firm*—Dorsey & Whitney LLP

(57) ABSTRACT

The present invention provides an auto-injection device including a housing, a container from which a product is dispensed by advancing a piston, the container shiftably accommodated by the housing and carrying a needle, and a drive unit including a driven member, wherein the driven member is shiftably accommodated by the housing and, during an auto-injection, is adapted for inserting the needle and advancing the container to a predetermined frontal position in relation to the housing and advancing the piston within the container for dispensing of the product, wherein the driven member remains uncoupled with the piston until the container reaches its frontal position, and upon the container reaching its frontal position, the driven member detaches from the container and couples with the piston for advancing the piston within the container.

16 Claims, 4 Drawing Sheets

U.S. PATENT DOCUMENTS

| | | |
|---|---|---|
| 5,114,406 | 5/1992 | Gabriel et al. . |
| 5,279,579 | 1/1994 | D'Amico . |
| 5,279,585 | 1/1994 | Balkwill . |
| 5,292,314 | 3/1994 | D'Alessio et al. . |
| 5,295,976 | 3/1994 | Harris . |
| 5,320,609 | 6/1994 | Haber et al. . |
| 5,336,183 | 8/1994 | Greelis et al. . |
| 5,338,311 | 8/1994 | Mahukar . |
| 5,370,629 | 12/1994 | Michel et al. . |
| 5,472,430 | 12/1995 | Vaillancourt et al. . |
| 5,496,293 | 3/1996 | Huggenberger . |
| 5,514,097 | 5/1996 | Knauer . |
| 5,527,294 | 6/1996 | Weatherford et al. . |
| 5,549,558 | 8/1996 | Martin . |
| 5,549,575 | 8/1996 | Giambattista et al. . |
| 5,573,510 | 11/1996 | Issacson . |
| 5,582,598 | 12/1996 | Chanoch . |
| 5,591,136 | 1/1997 | Gabriel . |
| 5,591,138 | 1/1997 | Vaillancourt . |
| 5,593,390 | 1/1997 | Castellano et al. . |
| 5,609,577 | 3/1997 | Haber et al. . |
| 5,629,299 * | 5/1997 | Brown et al. .......................... 514/58 |
| 5,643,214 | 7/1997 | Marshall et al. . |
| 5,658,259 | 8/1997 | Pearson et al. . |
| 5,674,204 | 10/1997 | Chanoch . |
| 5,679,111 | 10/1997 | Hjertman et al. . |
| 5,725,508 | 3/1998 | Chanoch et al. . |
| 5,728,074 | 3/1998 | Castellano et al. . |
| 5,743,872 * | 4/1998 | Kelly ...................................... 604/49 |
| 5,743,889 | 4/1998 | Sams . |
| 5,788,673 * | 8/1998 | Young et al. ......................... 604/131 |
| 5,807,346 | 9/1998 | Frezza . |
| 5,957,897 * | 9/1999 | Jeffrey .................................. 604/223 |

* cited by examiner

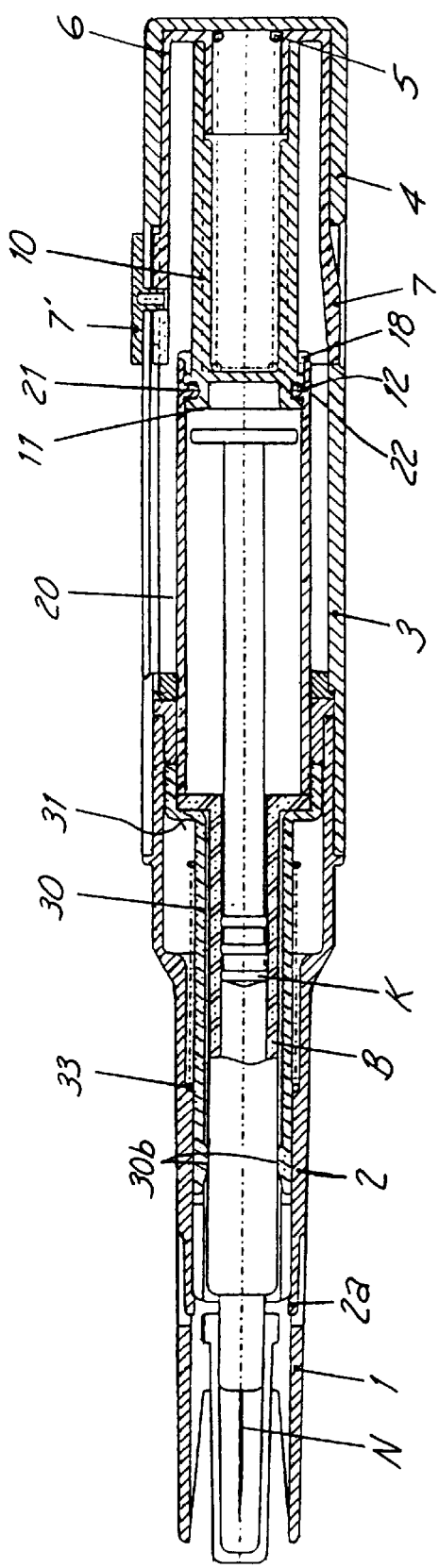
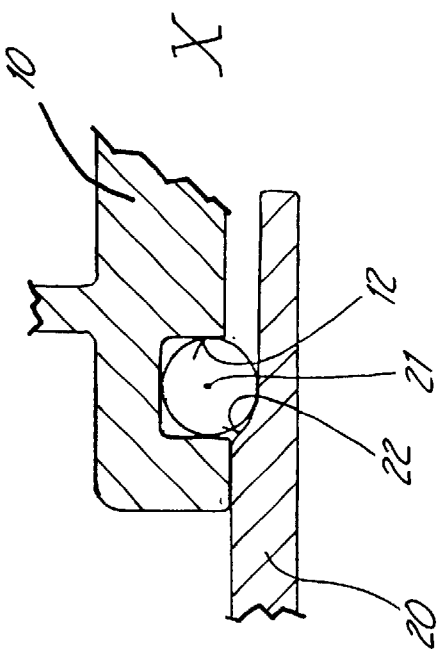
Fig. 1a
Fig. 1b

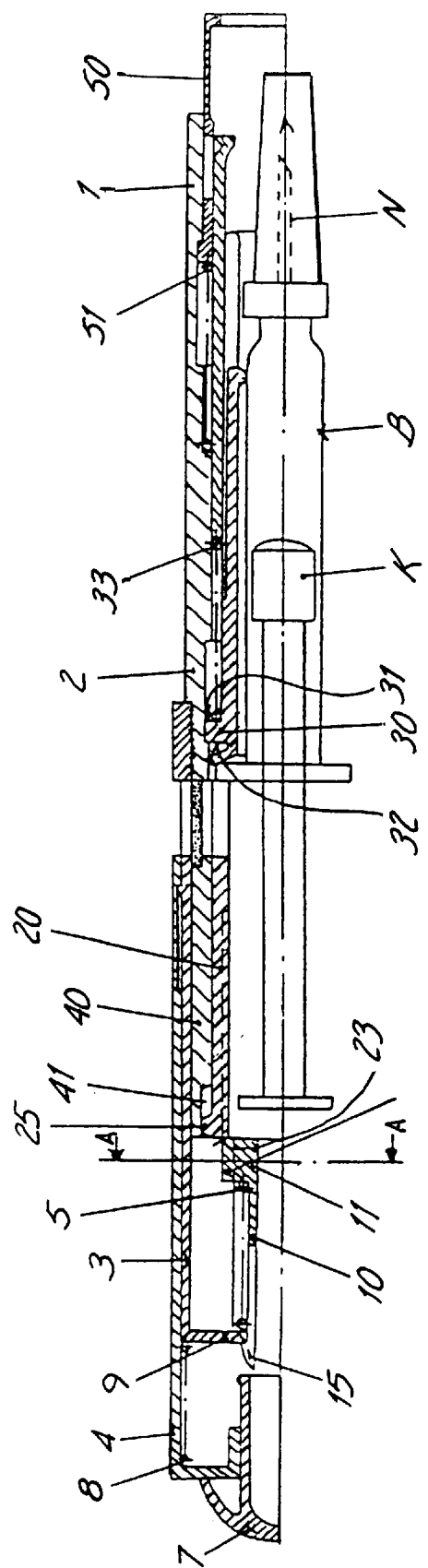
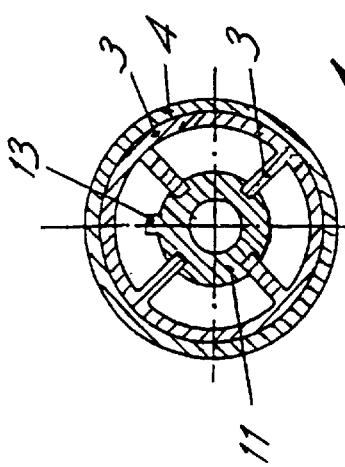

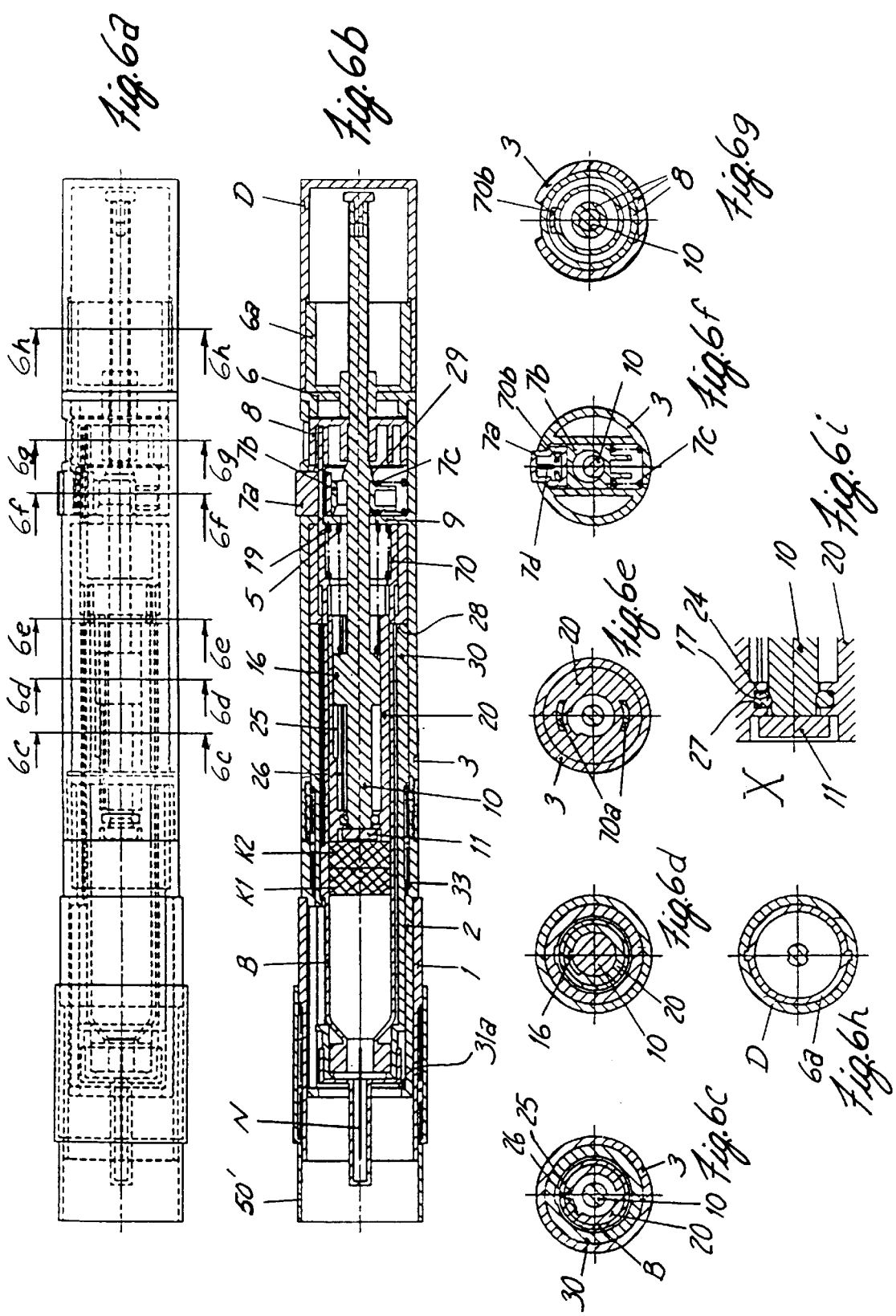

AUTOMATIC INJECTION DEVICE

RELATED APPLICATIONS

This application claims the priority of German Patent Application No. 198 22 031.6 filed May 15, 1998, which is incorporated herein by reference.

BACKGROUND OF THE INVENTION

The invention relates to an auto-injection device. Such auto-injection devices are used for the administration of products, in particular medically or cosmetically effective fluids. For administration, an injection needle through which the product is dispensed is automatically inserted into a tissue by a predetermined path length after having been triggered by a drive mechanism.

Auto-injection devices typically comprise a housing, a container shiftably or moveably accommodated by the housing from which a product to be administered is dispensed through a needle arranged at an outlet of the container by advancing a piston, and a driven member of a drive unit, the driven member being shiftably accommodated by the housing. During auto-injection, the driven member advances the container in relation to the housing in the forward direction to a predetermined frontal position for inserting the needle, and the driven member advances the piston within the container for dispensing the product. When the container has reached its frontal position during an auto-injection, the needle has been advanced by a predetermined path length with respect to the container. The path length may also determine the penetration depth of the needle.

Auto-injection devices of the described design are known from U.S. Pat. Nos. 5,514,097; 159,192; and 5,643,214; as well as European Patent No. 0 516 473 B1. In the known auto-injection devices, the container is advanced together with the attached needle by a pressure which the driven member exerts on the piston.

SUMMARY OF THE INVENTION

It is an object of the invention to provide an auto-injection device ensuring that a product to be administered is only dispensed upon an injection needle having been completely advanced when being inserted into a tissue.

In one embodiment, the present invention provides an injection device comprising a housing, a container shiftably accommodated by said housing, carrying a needle and accommodating a moveable piston, and a drive unit comprising a driven member shiftably accommodated by said housing wherein, during an injection, the driven member is adapted for inserting said needle and advancing said container to a predetermined position in relation to said housing, at which said predetermined position said driven member is decoupled from said container and coupled with said piston for moving said piston within said container.

In one embodiment, an auto-injection device for administering a product in accordance with the present invention comprises at least a housing, a container shiftably accommodated by said housing and a driven member of a drive unit. The product is dispensed from the container through a needle at an outlet of the container by advancing a piston arranged in the container. The driven member is shiftably accommodated by the housing. During an auto-injection for inserting the needle, the driven member advances the container to a predetermined frontal position in relation to the housing and advances the piston within the container for dispensing all or part of the product. The driven member is not coupled with the piston until the frontal position of the container is reached. Upon reaching the frontal position of the container, it is decoupled from the container and coupled with the piston for advancing the piston within the container.

Accordingly, advancement of the container for inserting the needle is not effected by the piston, i.e., during this phase of movement there is no drive connection between the driven member and the piston. This rules out the possibility that the product may be dispensed prematurely during advancement of the container by even a small forward movement of the piston within the container, i.e., in relation to the container. By disengaging, i.e., decoupling, the driven member from the container and engaging it, i.e., coupling it, with the piston not earlier when the container is in its frontal position, the piston will only be advanced within the container upon the needle being inserted into the tissue to the required depth. The separation of the advancement of the container and the advancement of the piston within the container at the side of a drive mechanism increases dosing accuracy, due to pressure on the piston not being applied during advancement of the container, thus preventing the product from being dispensed prematurely.

The driven member may act directly on the container for advancement of the container.

In one embodiment, a transfer member is provided, which is driven along by the driven member during forward advancement, thus acting on the container and/or the container holder and resulting in advancement of the container. The transfer member may also be a container holder, but may be designed as a part separate therefrom.

The disengageable coupling may exist between the driven member and the transfer member. After disengaging the coupling in the frontal position of the container, a further advancement of the driven member, i.e., for advancement of the piston, does not result in any further advancement of the transfer member. The driven member now may be disengaged from the transfer member with respect to its own forward movement. It only pushes against the piston and drives the piston forward in the container. In one embodiment, the transfer member is accommodated by the housing shiftably in and against the direction of advancement of the piston.

In one embodiment, the driven member and the container are coupled to each other by a purely positive locking. In another embodiment, the coupling includes a non-positively locked connection between the driven member and the container. Hybrid locking connections may also be used.

A positively locked connection of the driven member and the transfer member may be formed by the driven member being connected to a first coupling means and the transfer member being connected to a second coupling means, with these two coupling means together forming a bolt-and-lock connection which is released at that point in time at which the container reaches its frontal position. The first coupling means may be rigidly connected to the driven member and effecting an advancement of the transfer member by pushing against a stop face of the transfer member. In one embodiment, the first coupling means is simply a cam projecting from the driven member. In the course of unlocking and the ensuing decoupling of the driven member from the transfer member, the cam, acting like a blocking bolt, is brought into coverage with a recess ending in the stop face, with the cam no longer pushing against the stop face and, so-to-speak, opening the lock by falling into the lock. The driven member is released from the transfer member, thus also releasing the coupling with the container, enabling the driven member to move further forward, in relation to the transfer member. In the course of this movement in relation to the transfer member, the driven member comes into pushing contact against the piston, thus effecting coupling of the driven member with the piston. The blocking bolt could also be connected to the transfer member and the lock to the driven member.

The decoupling of the driven member from the transfer member is may be effected by rotation of one of the two members in relation to the other. This relative rotation may be effected around a rotational axis parallel to the shift direction. The relative rotation is generated compulsorily due to advancement, in one embodiment by a coulisse guiding formed between the member to be rotated and the housing. Although a frictional force generated during the rotation may be used for selectively affecting the forward speed of the driven member and the transfer member, the coupling as such, i.e., blocking and releasing, is purely a positive locking effect.

In another embodiment, a combined positive and non-positive locking connection is used for coupling and decoupling the driven member with and from the container and with and from the piston. In this embodiment, the coupling may be formed between the driven member and a transfer member, although coupling directly with the container would also be possible.

The coupling may, in one embodiment, be formed by a snap coupling. During advancement of the driven member, a snapper (which also may be referred to as a snapper or snap member) pushes against a contact pressure surface, thus advancing the container. When the container has reached its frontal position, in which it is positioned against a stop in relation to the housing, the snap coupling is released by the drive force continuing to be exerted to the driven member. The driven member is then coupled to the piston and advanced further, free from the container and/or free from a transfer member. A slight supporting push upon reaching the frontal position of the container may certainly be desirable.

One or more of the means forming the coupling may be flexible made from products such as elastic. One or more snappers may be directly formed on the driven member, which is pushing therewith against a stop face on the container or the transfer member, should this be used. Such snappers may also be provided on the transfer member.

A third coupling means may also be used to provide the coupling. The third coupling may be flexible, such as a flexible elastic. The third coupling means may also be a flexible washer, in particular a spring washer, clamped between two opposite faces, one of the driven member, and the other of the transfer member, and being pushed over one of these two contact pressure surfaces as soon as the container has reached its frontal position.

The invention may also be advantageously used in such auto-injection devices in which the container is formed by a so-called multi-chamber ampoule. With these multi-chamber ampoules, the product to be administered is obtained only upon assembling the device by mixing the contents of several chambers which are separate from each other. Each of the chambers arranged in line is closed at its rear by a piston shiftably accommodated within the container. For mixing, a mixing member is pushed against the rear piston and pushes, in the course of its advancement within the container, each of the pistons forward to the most frontal piston. During advancement, a connection is made to each respective adjacent frontal chamber, thus displacing the content of each rear chamber to the respective adjacent chamber in front of it.

According to the invention, the mixing member, which may be a mixing tube, also forms the transfer member for advancement of the container. According to the invention, the mixing member has been allocated a dual function. From a design point of view, this may be achieved by the mixing member comprising a web radially extending outwards, preferably having the shape of a circumferential shoulder, for pushing against the rear face of the container or, if preferred, against a rear contact pressure surface of the container holder, the container holder in its forward movement being forced by the mixing member to take the container along with it. The frontal position of the container may be defined by the container holder striking the housing.

The housing may enclose both the container and the entire drive unit and may have the shape of a sleeve. In its most general design, however, the housing serves as a base section only, in relation to which displacement of the container and displacement of the driven member of the drive unit is effected and must therefore not exclusively be seen as a surrounding housing, although such an embodiment is possible.

Other features and advantages of the injection devices and methods of the present invention will become more fully apparent and understood with reference to the following description and appended drawings and claims.

BRIEF DESCRIPTION OF THE DRAWINGS

FIG. 1a is a longitudinal view of an auto-injection device in accordance with the present invention;

FIG. 1b is a view of the coupling of the transfer member and driven member of the embodiment of FIG. 1a;

FIG. 2a is a longitudinal view of a second embodiment of an auto-injection device with a positive locking coupling;

FIG. 2b is a cross sectional view along line A—A of FIG. 2a;

FIG. 3 is a plane view of the transfer member of the embodiment of FIG. 2a;

FIG. 4 is a view of a portion of the embodiment of FIG. 2a;

FIG. 5 is a second view of a portion of the embodiment of FIG. 2a;

FIG. 6a is a longitudinal view of an embodiment of an auto-injection device of the present invention including a dual-chamber ampoule and a mixing tube designed as a transfer member;

FIG. 6b is a second longitudinal view of the embodiment of FIG. 6a;

FIG. 6c is a cross sectional view along line C—C of FIG. 6a;

FIG. 6d is a cross sectional view along line D—D of FIG. 6a;

FIG. 6e is a cross sectional view along line E—E of FIG. 6a;

FIG. 6f is a cross sectional view along line F—F of FIG. 6a;

FIG. 6g is a cross sectional view along line G—G of FIG. 6a;

FIG. 6h is a cross sectional view along line H—H of FIG. 6a; and

FIG. 6i is a view of a portion of the embodiment of FIG. 6a;

DETAILED DESCRIPTION

Figure 3:
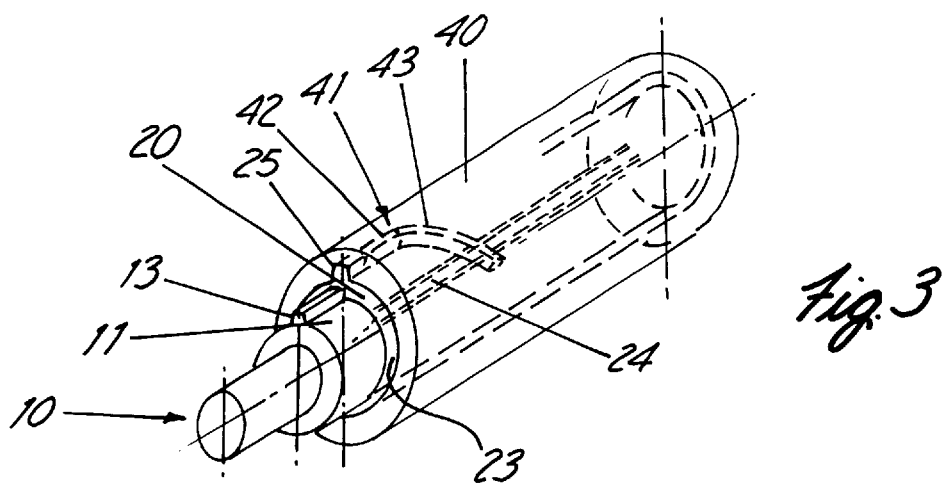

The accompanying Figures and this description depict and describe embodiments of the automatic injection device and method of the present invention. With regard to means for fastening, mounting, attaching, coupling or connecting the components of the present invention to form the device and system as a whole, unless specifically described otherwise, such means are intended to encompass conventional fasteners such as machine screws, nut and bolt connectors, machine threaded connectors, snap rings, hose clamps such as screw clamps and the like, rivets, nuts and bolts, snap fittings, toggles, pins and the like. Components may also be connected by adhesives, glues, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

FIG. 1a is a longitudinal section of an auto-injection device which is an injection pen.

The pen comprises a hollow cylindrical housing, which is a circular cylindrical shape in the embodiment of FIG. 1a, comprising a needle protection 1 at its frontal end, followed by a frontal housing sleeve 2 and an adjacent rear housing sleeve 3 including a housing cap 4, completing the rear housing sleeve 3 at the rear. The frontal housing sleeve 2 surrounds a cylindrical container B, which may be held in a container holder 30 coaxially centered to the central longitudinal axis of the housing. The container holder 30 is also sleeve-shaped, ending at its front in centering tongues which press against the circumferential edge of the container B and center the same in the frontal housing sleeve 2. The container holder 30 is shiftable back and forth along the central longitudinal axis of the housing. During forward advancement of the container holder 30, the container B arranged therein is also shifted. Thereby, an injection needle N, arranged at an outlet of the frontal end of the container B, is advanced and inserted into and under a patient's skin during an auto-injection.

The container B comprises a piston K, shiftable along the central longitudinal axis of the container B. When shifting the piston K in the forward direction, a product in the container B, in one embodiment a liquid active substance, such as insulin, is displaced through the outlet into and through the injection needle N for dispensing the product. A piston rod is projecting from the rear of the piston K over the rear edge of the container.

The container B is widened by a flange along its rear edge. The container holder 30 is also widened accordingly at its rear end and continued beyond the container over a distance by a widened section having the shape of a sleeve. In assembled condition, the rear widened section of the container B rests on the shoulder face of the container holder 30 facing this widened section. An external jacket face of the container holder 30 is surrounded by a compression spring acting as a restoring element 33 being in contact with its frontal end with a shoulder face of the frontal housing sleeve 2, from where it projects almost to a counterface 31, formed by the widened section of the container holder 30, said counterface facing said shoulder face of the frontal housing sleeve 2. During advancement of the container holder 30 and therefore of the container B, the compression spring 33 is compressed between the two faces facing each other, thus cushioning the forward movement of the needle N during insertion. During advancement, the face 31 strikes against a shoulder face formed in the area of a stepped widened section of the frontal housing sleeve 2. The stop of the shoulder face 31 of the container holder 30 defines a frontal position of the container B and therefore the length by which the needle N projects over the frontal edge of the housing in frontal position of the container B, simultaneously also specifying the insertion depth of the needle N if the pen is correctly placed on the skin.

A drive unit for advancement of the container B and the piston K within the container B is formed by a drive element 5 designed as a compression spring, and a driven member 10. Drive force could also be applied by a pressurized medium. The driven member 10 may be sleeve-shaped, including a rearwardly open sleeve pot, completed by a base. The driven member 10 is extended in sleeve shape at its frontal end toward the piston rod beyond the base over a relatively short distance. The extension is formed by a plunger 11 for pushing against the piston rod and advancing the piston K within the container B.

In the initial position of the injection pen shown in FIG. 1a, there is no direct pushing of the plunger 11 against the piston rod. A small clearance remains between the plunger 11 and the rear face of the piston rod. In the initial position of the pen, in which the container B is in its rear shift position, the driven member 10 is coupled to the container B. The driven member 10 is directly coupled to a transfer member 20 which in turn directly affects the container B.

The transfer member 20 could alternatively directly affect the container holder 30. In this case a drive dog would have to be provided between the container holder 30 and the container B. In principle, the driven member 10 could push directly on a container B or a container holder 30 in order to advance the needle N.

As shown in FIG. 1b, the transfer member 20 is formed by a sleeve body, with a circumferential shoulder 22 formed in its rear section by reducing the cross-sectional area, the shoulder 22 acting as a frontal contact pressure surface for an elastic spring washer 21. The elastic spring washer 21 is held blocked against shifting in relation to the driven member 10 in a groove surrounding the external jacket surface of the driven member 10 within the area of the plunger 11. The washer 21 may be designed as a fully closed, soft elastic washer, but may also be made of a hard material, such as plastic or metal, open at one point, to allow the ends of the washer 21 facing each other to be moved toward each other over a distance, thus allowing the diameter of the washer 21 to be reduced. The flexible washer 21, the shoulder 22 and the wall 12 of the groove facing the shoulder 22 form a releasable positive and non-positive locking coupling between the driven member 10 and the transfer member 20. The washer 21, as compression and coupling means, could also be designed as a bead on the driven member 10 or the transfer member 20, which would end in such an embodiment at the front in bendable tongues.

The driven member 10 is held against the pressure of the drive element 5 in its initial position shown in FIG. 1a by a blocking and release sleeve 6 by means of a release tab 7 formed on the blocking and release sleeve 6. The connection is released by pushing the release tab 7 inward.

For injection of the product, the pen is positioned on the skin with the frontal edge of the needle protection 1 under light pressure after removing the needle protection. Then the release tab 7 is pressed, thus releasing the connection between the release sleeve 6 and the housing. The driven member 10 is then advanced in a forward direction within the housing under the pressure of the drive element 5. The coupling transfers the forwardly shifting force of the driven member 10 from the groove wall 12 to the washer 21 and from there to the shoulder 22 and therefore to the transfer member 20. The transfer member 20 pushes with its frontal face against the container B and the container holder 30 which are advanced in the housing under the contact pressure of the transfer member 20, initially without resistance apart from wall frictional forces. The needle N, pointing accurately in the forward direction, is pushed forward beyond the frontal edge of the needle protection 1 and penetrates into the tissue. The advancement of the container B and therefore the penetration depth of the needle N are limited by pushing the shoulder face 31 of the container holder 30 against the counterface on the housing. The container B is now in its frontal position.

During the advancement of the container holder 30 and the container B, there exists the engagement, i.e., the drive coupling, of the driven member 10 and the transfer member 20. The coupling is designed to be released upon the container B reaching its frontal position (or forwardmost extent of travel in the direction of the needle, which frontal or forwardmost position may be adjustable or selectable in some embodiments).

This is achieved by the dimensioning of the flexible washer 21 and the shaping of the shoulder 22, serving as a stop for the washer 21. The shoulder 22 extends in the forward direction obliquely or in a curve from the wider rear section to the narrower frontal section of the transfer member 20.

The flexible washer 21 is round in cross section. In principle, the shape of the cross section of the washer 21 and the shape of the shoulder 22 need to be adjusted to each other only in such a manner that the flexible washer 21 does not shift over the shoulder 22 prior to the container having reached its frontal position. For this the coupling has to transfer at least the reaction force existing during advancement of the container B and the force required for inserting the needle N, and must not block after the container has reached its frontal position but being securely released. The adjustment of the coupling is at its optimum when released, and is subject to minimum jerking.

When the coupling, formed by the coupling means 12, 20, 21 and 22, has been released or even during release, the driven member 10, advancing further subject to the pushing of the drive element 5, comes into pushing contact with the piston rod, thus being coupled to the piston K, which advances within the container B under the contact pressure applied by the driven member 10, thus displacing product and dispensing it through the needle N.

In order to compensate for a decrease in power of the drive element 5, which accompanies the advancement of the driven member 10, the internal jacket face of the transfer member 20 may be conically widened. The washer 21 would be subject to frictional forces which decrease with the advancement of the driven member 10 due to such widening. This feature of controlled dampening of the drive force would benefit from the elasticity of the washer 21 or some other contact pressure means having the same effect, i.e., such as a damper for compensation.

As an alternative to this compensation based on the control of sliding frictional forces, a decrease in drive force may also be compensated for pneumatically. In the case of pneumatic compensation, the space surrounded by the jacket faces of the driven member 10 and the transfer member 20 may be sealed hermetically as far as possible. The guide ring 18 inserted at the rear end of the transfer member 20 may be designed as a sealing washer to the driven member 10, which itself would form a piston. In addition, the slideways formed between the internal jacket of the transfer member 20 and the opposing face of the plunger 11 could be designed as sealing faces. This would form a cavity between the external jacket face of the driven member 10 and the internal jacket face of the transfer member 20, with the cavity increasing during advancement of the driven member 10.

Only a calibrated passage would have to be provided in the guide ring 18 designed as a seal, through which a medium, such as air, could flow into the otherwise sealed cavity. The depression generated by the advancement of the driven member in this cavity would be subject to delayed compensation only, such that the forward speed of the driven member 10 may remain constant over the entire stroke of the piston K.

The spring 33 may have a cushioning effect and may therefore delay the forward movement of the container holder 30 together with the container B, although the container holder 30 and the container B are moved initially over part of the distance which is not impeded by the spring 33, due to the shoulder 31 of the container holder 30 only pushing against the spring 33 after completing the movement. Forward movement over the remaining distance to the frontal container position may then be decelerated by the lower returning force of the spring 33 versus the force exerted by the drive element 5. As desired, a fast penetration of the needle followed by decelerating its forward speed in the lower tissue layers is achieved. Stop tabs 2a, provided on the frontal housing sleeve 2 retain the container holder 30 in its rear position. Under the pressure of the drive element 5 and therefore the container holder 30 upon being released, the stop tabs 2a, however, will yield. By means of a tensioning handle 7' projecting into the housing, the blocking and release sleeve 6 and the driven member 10, which are shiftably accommodated in the housing in the rear position, are returned to their rear position and retensioned. The driven member 10 and the sleeve 6 are suitably connected to each other. In the rear position a new container B can now be inserted.

FIG. 2a is a longitudinal section and FIG. 2b is a cross section along line A—A FIG. 2a of a second embodiment of an auto-injection device, again constituting a pen. In this pen, the drive connection between the driven member 10 and the container B and the driven member 10 and the piston K is purely effected by positive locking and releasing. As an additional difference, this embodiment may contain a needle safety sleeve covering the needle N after retraction from the tissue, thus reducing the risk of injury during subsequent handling.

The housing is also formed by a frontal housing sleeve 2 and a rear housing sleeve 3. In this embodiment, the needle protection 1 is an integral part of the frontal housing sleeve 2. In the hollow cylindrical housing, again, a container holder 30 in which a container B filled with a product to be administered is kept in a centered position, supported smilingly in a shiftably position back and forth along the longitudinal axis of the housing. During advancement for inserting the needle N, the frontal stop face 31 of the container holder 30 is advanced against a stop formed by the housing, thus defining the frontal position of the container B and the insertion depth of the needle N. After injection, the two housing sleeves 2 and 3 are unscrewed, thus releasing the container B and the container holder 30 from the transfer member 20 and returning the container holder 30, subject to the pressure applied by the restoring element 33, which may be designed as a restoring spring, with a rear stop face 31 against a stop face formed by the housing into its rear position, i.e. the initial position. In this rear position a new container B can be inserted. After screwing the two housing sleeves 2 and 3 together, the pen of FIG. 2 is ready for the next injection.

As described for the embodiment of FIG. 1, the driven member 10 of the pen of FIG. 2 acts on the container via a transfer member 20. In the same way, the transfer member 20 could act on the container holder 30, in turn driving it along with the container B. The advancement of the piston K within the container B is due to direct contact pressure of the plunger 11 of the driven member 10 being applied to the piston rod projecting rearwardly out of the container B, the piston rod being attached to the piston K or moulded as an integral part of the piston K, starting from its rear.

FIG. 3 is a drawing of the driven member 10, the transfer member 20 and a guide means 40 according to their position in FIG. 2a. With reference to coupling and releasing the driven member 10 to and from the transfer member 20, reference is also made to the drawing of FIG. 3.

The driven member 10 is formed by a fully cylindrical base body, comprising a plunger 11 with a widened cross section. Again, the drive element 5 is formed as a compression spring, surrounding a cylinder shaft section of the driven member 10. In the initial position of the pen, the drive element 5 is clamped between the thickened plunger 11 and the ribs 9 projecting from the rear housing sleeve 3 radially towards the inside and cylindrical shaft section. The driven member 10 is held in initial position by means of snappers 15.

Several snappers 15 may project from the cylinder shaft section as an extension of the cylinder shaft section of the driven member 10 and may grip behind the ribs 9 extending radially inwards.

A rib or cam 13 extends from the external jacket face of the plunger 11. With its cam 13 the driven member 10 is stopped against a rear face 23 of the transfer member 20. The transfer member 20 is formed by a simply hollow cylindrical sleeve, preferably a circular cylindrical sleeve, from the external jacket face of which in a rear section a cam 25 extends radially outward. A release groove 24, as shown in FIG. 3, is relieved in the internal jacket face of the transfer member 20, with the release groove 24 extending in the longitudinal direction of the transfer member 20 and ending in the rear face 23. The minimum size of said groove 24 may be adapted such that the cam 13 of the driven member 10 can engage in the groove 24.

The transfer member 20 is shiftably arranged in a longitudinal direction and rotatable about its longitudinal axis in a hollow cylindrical, perhaps circular cylindrical sleeve. This sleeve forms a guide means 40, or simply a guide, for the transfer member 20 such that a shifting movement of the transfer member 20 in relation to the guide means 40 is converted into rotation of the transfer member 20 around its longitudinal axis in relation to the guide means 40, i.e., the shifting movement being superimposed by rotation. In this embodiment, the guide means 40 is designed as a separate sleeve, accommodated in the housing and secured against rotation and shifting. In principle, it could form an integral part of the housing, in this embodiment with the rear housing sleeve 3, which may, however, result in increased production expenditure.

The relative rotation of the transfer member 20 in relation to the guide means 40 and the driven member 10 guided straight and secured against rotation in the housing, is effected by means of a coulisse guiding being formed between the transfer member 20 and the guide means 40.

The design of the coulisse guiding, as shown in FIG. 3, provides a guide groove 41 for the cam 25, the guide groove 41 being relieved in the internal jacket face of the guide means 40 opposite to the cam 25 of the transfer member 20. The guide groove 41 comprises a rear straight groove section 42 and a chamfered second groove section 43 extending in a curve, i.e., the second groove section 43 comprises a component pointing transversally to the forward direction of the transfer member 20, and the second groove section 43 may have an end which is simply chamfered. In the initial position, the cam 25 is positioned in the groove section 42.

Referring again to FIG. 2a, a release mechanism may comprise an external sleeve 4, a release button 7 and a restoring spring 8. The external sleeve 4 may surround the rear section of the rear housing sleeve 3, the external sleeve 4 being shiftable back and forth on the external jacket face of the rear housing sleeve 3 along its longitudinal axis. The release button 7 is inserted into a central opening of the rear face of the external sleeve 4, projecting through this opening with an internal sleeve extending close to the snappers 15 of the driven member 10.

The pen of FIG. 2a may be pressed against the skin for injection such that a needle safety sleeve 50 being shiftable within the frontal section of the frontal housing sleeve 2 in the longitudinal direction is shifted against the pressure of a restoring unit 51, into the frontal housing sleeve 2 below the needle protection 1. In this condition, the needle N is still set behind the frontal edge, formed by the frontal ends of the needle protection 1 and the needle safety sleeve 50.

Inserting the needle N and dispensing the product are effected by pressing the release button 7 in the longitudinal direction of the pen toward the driven member 10 and its snappers 15. The internal sleeve of the release button 7 may then be pushed over the rear ends of the snappers 15 which in turn are bent elastically and radially inward toward each other, whereby the engaging connection is released from the ribs 9 of the housing.

The pressure applied by the drive element 5 is transferred by the released driven member 10, the cam 13 of which is pressed against the rear face 23 of the transfer member 20, to the transfer member 20, which in turn presses its frontal face against a rear flange face of the container B. The container B presses against the container holder 30 by the frontal face of the same flange, which in turn presses against a blocking sleeve 60, which cannot be shifted in relation to the housing, by means of the restoring unit 33. The pressure force of the restoring element 33, however, is low in comparison with that of the drive element 5, whereby the driven member 10, the transfer member 20, and the container holder 30 together with the container B are advanced along the longitudinal axis of the housing within the housing under the pressure of the drive element 5.

During this advancement the cam 25 of the transfer member 20 slides in its guide groove 41. As soon as the cam 25 enters the second groove section 43 during advancement, the transfer member 20 is forced, due to the transversal component of the second groove section 43, into rotation around its longitudinal axis. The course of the guide groove 41 has been selected such that the release groove 24 which is relieved in the transfer member 20 and ends in the face 23, comes into an overlapping coverage with the cam 13 due to the forced relative rotation in relation to the housing and the driven member 10.

As soon as the release groove 24 overlaps the cam 13, the driven member 10 is decoupled from the transfer member 20. The course of the guide groove 41 has been selected such that the overlapping coverage is established as soon as the frontal stop face 31 of the container holder 30 pushes against the stop of the housing, the container B being at the same time in the frontal position. The decoupling, i.e., the release, allows the driven member 10 to advance further in relation to the transfer member 20 under the pressure of the drive element 5, pushing against the piston rod to displace the piston K within the container B under the direct contact pressure of the driven member 10 until the product has been dispensed.

Inserting the needle N is set as desired by the course of the guide groove 41. Initially, the needle N is inserted very rapidly since the guide groove 41 extends straight in the forward direction during a first part of the forward movement of the transfer member 20, thus not posing any resistance against the advancement of the transfer member 20. Penetration speed is decelerated as the needle penetrates, due to the guide groove 41 now extending also transversely in the forward direction, spirally in the embodiment, whereby the transfer member 20 within the guide section 43 therefore is exposed to a frictional force during advance, said frictional force being dependent on the slope of the guide section 43. In addition, the speed at which the needle N is inserted is reduced by the increasing restoring force of the restoring element 33.

Figure 4:
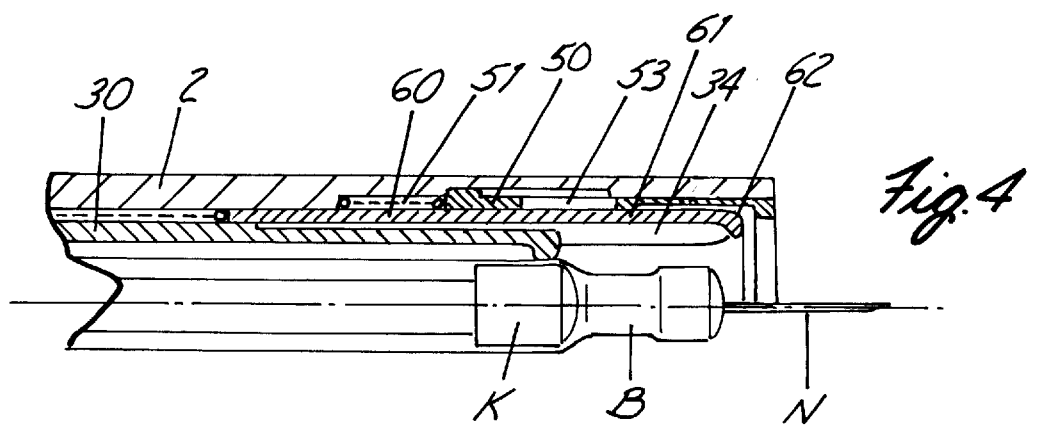
Figure 5:
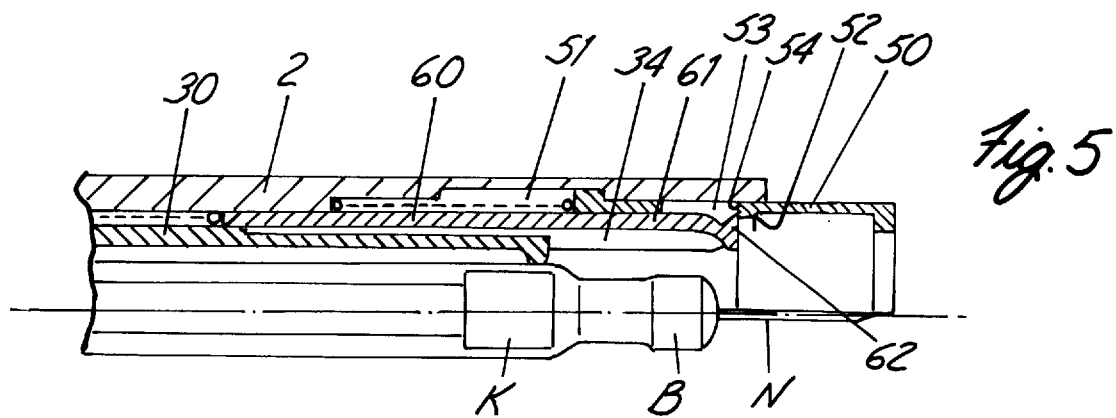

FIGS. 4 and 5, together with FIG. 2 show the mode of operation of the needle safety unit, preventing the needle N from freely projecting from the housing after retracting it from the tissue and possibly being broken or causing injuries due to careless handling. The major characteristic of the needle safety sleeve is blocking of the needle safety sleeve 50 in relation to the housing after retraction of the needle N, thus preventing it from being pushed into the housing. An arrangement where the needle safety sleeve in pushed over the housing externally could also be imagined.

FIG. 4 shows the frontal section of the pen of FIG. 2 in the frontal position of the container B. The needle safety sleeve 50 has been pushed to its rear shift position in relation to the housing sleeve 2 against the pressure of the restoring element 51. The needle N projects over the housing and the needle safety sleeve 50 by the desired length.

The needle safety sleeve 50 comprises a rear stop face and a frontal stop face, limiting the shifting path of the needle safety sleeve 50 in relation to the frontal housing sleeve 2 in and against the forward direction. When the needle safety sleeve 50 is moved in either direction, it passes over the blocking sleeve 60, comprising a hook 62 at its frontal end, projecting obliquely or curved outward. In an internal jacket section that slides over the hook 62, the needle safety sleeve 50 is of a slightly widened diameter, corresponding approximately to the length of its maximum shifting path. A transitional section 52 between this widened internal frontal cross section and the subsequent internal cross section is chamfered, thus allowing the needle safety sleeve 50 to slide over the hook 62, subject to the pressure of the restoring element 51, beyond the end of the transitional section 52. In a central section behind the transitional section 52, the needle safety sleeve 50 is provided with longitudinal slots 53, the frontal faces 54 of which, as best seen in FIG. 5, form the stop faces for one hook 62 each.

The blocking sleeve 60 ends in a number of elastic and flexible tongues 61, evenly distributed over the circumference of the sleeve, to the free frontal ends of which the hooks 62 are moulded. The container holder 30 also ends in tongues 34 towards its free frontal end. During advancement of the container holder 30, its tongues 34 are positioned below the tongues 61 of the blocking sleeve 60. Each of the tongues 61 is therefore supported radially inward and can no longer be bent in the frontal position of the container. The tongues 61 are not only supported by the tongues 34, but in addition pushed radially outwards. In comparison with the tongues 61, the tongues 34 may be rigid.

After retraction of the needle N, the needle safety sleeve 50 is pushed forward again by the restoring element 51, pushing over said hook 62 due to the chamfer of the surface 52 and/or the appropriate chamfer of the hook 62, the end of which may be elastic and flexible. However, as soon as the needle safety sleeve 50 has been advanced so that its stop face 54 is positioned in front of the hook 62 when seen in the forward direction, it is blocked against shifting backward by the hook 62, stopping against the stop face 54. The hook 62 and the needle safety sleeve 50 are in contact with stop faces which are directed vertically to the shift direction. After injection, the needle N is protected by the needle safety sleeve 50, as shown in FIG. 5 in the safety position.

The container holder 30 may therefore be simultaneously used as a shiftable support for the elastic blocking means 62 and according to the invention fulfils a double function, i.e., holding the container and blocking the needle safety sleeve 50. The needle safety sleeve 50 does not require the design of the auto-injection device according to the invention, although this could be combined with the same. It may also be applied advantageously in generic auto-injection devices or even unchanged in injection devices in which insertion of the needle N by advancement of the container B in relation to the housing is effected manually.

FIGS. 6a–6i comprise a longitudinal section and views a plan view of an auto-injection pen, in which the driven member 10 is coupled to the container B and the piston K, subject to positive and non-positive locking. The coupling may in its effect be compared with that of the pen of FIG. 1. In the following description, reference is also made to the cross sections (FIGS. 6c–6h) of the plan view (FIGS. 6a and 6b) and FIG. 6i.

The container B of the pen of FIGS. 6a–6i may be a so-called dual-chamber ampoule in which two product components contained in two in-line chambers are separated, in delivery condition of the container B, by a frontal piston K1, are initially mixed with each other by advancement of a rear piston K2 against the frontal piston K1. The frontal chamber in the delivery configuration generally contains a powdered active substance, whereas a carrier fluid is stored in the chamber formed between the two pistons K1 and K2.

In the condition shown in FIG. 6b, the two components have been completely mixed by advancement of the rear piston K2 against the frontal piston K1, in the frontal chamber located between the piston K1 and the outlet of the container B. Again, the housing comprises a frontal and rear housing sleeve 2 and 3, firmly attached to each other, for instance, by a screw or a plug-Page type connection. A cap 4 is plugged into the rear housing sleeve 3. The frontal housing sleeve 1 is extended toward the front by a needle protection 1 and a needle safety sleeve 50' which is pushed back for inserting the needle N against a restoring force, returning to the advanced position after injection.

The container B is pushed into a container holder 30 up to the stop and kept in the entered position. The container holder 30 is shiftably arranged in the forward direction within the housing against the pressure of the restoring element 33.

Advancement of the rear piston K2 is effected upon assembling the frontal housing sleeve 2 to the rear housing sleeve 3. For this purpose, a mixing member 20, designed as a sleeve, is accommodated in the rear housing sleeve 3, secured against rotation. The mixing member 20 comprises a frontal sleeve section of an external diameter smaller than the internal diameter of the container B and a rear sleeve section widened in relation to the frontal sleeve section. The transition between these two sleeve sections is designed as a shoulder 28, radially projecting from the frontal sleeve section. The shoulder 28 extends all round. However, it may also be formed by one or more radially projecting webs. The rear face of the mixing member 20 contacts the webs 9 projecting radially inward from the rear housing sleeve 3, which webs may be designed as a circumferential wall. When assembling the device, i.e., upon screwing on the two housing sleeves 2 and 3, the mixing member 20, secured against shifting in this way in the rear housing sleeve 3, is introduced into the container B, which is open at the rear, and is pushed forward in the same, whereby it pushes the rear piston K2 forward toward the frontal piston K1 until the rear piston K2 has reached the position shown in FIG. 1a. In this position of the pistons K1 and K2, screwing the housing sleeves 2 and 3 together has also been completed.

The drive unit is arranged in the rear housing sleeve 3, the drive unit comprising the drive element 5, which may be designed as a compression spring, and the rod-shaped driven member 10, guided straight in the housing. The drive element 5 is clamped between the webs 9 and a circumferential shoulder face of the driven member 10, said shoulder face being provided in the forward direction of and facing to the web 9.

The driven member 10 is arranged rotatably around a central longitudinal axis of the housing, coinciding with its own central longitudinal axis, allowing rotation in either direction between two rotational positions. A dosing sleeve D, as shown in FIG. 6b, which extends the housing, is provided for rotating the driven member 10. In its rear section, projecting into the dosing sleeve D, the driven member 10 comprises guide grooves extending in the forward direction, into which a guide sleeve 6a and an indicator sleeve 8 engage. The guide sleeve 6a projects into the cap 4 and is not shiftable but is rotatable in relation to the cap 4. The indicator sleeve 8 is arranged in the housing rotatably but not shiftable in relation to the housing. The guide sleeve 6a may be connected to the dosing sleeve D securely against rotation, as best seen in section H—H (FIG. 6h). The guide sleeve 6a acts to transfer rotation of the dosing sleeve D to the driven member 10. The indicator sleeve 8, connected to the driven member 10 securedly against rotation, is used for indication of the rotational position of the driven member 10 and therefore indication of the set dose. For this purpose, markings are provided on its external circumference, in the embodiment two markings, i.e., one for each of the two final rotational positions of the driven member 10. These markings can be read through an opening in the housing. Both the indicator sleeve 8 and the guide sleeve 6a are used together with the mixing member 20 as a straight guide for the driven member 10.

In its rear initial position as shown, the driven member 10 is retained by a blocking and release mechanism. The blocking and release mechanism comprises a release means 7a, designed in one embodiment as a release button, acting transversally to the shift direction of the driven member 10 on a blocking means 7b. The construction and mode of operation of the blocking and release mechanism is best seen in the joint longitudinal section and cross section F—F (FIG. 6f).

The blocking means 7b may be formed by a sleeve body having a through-opening through which the driven member 10 projects. For straight guidance transversally to the forward and longitudinal direction of the driven member 10, the blocking means 7b is guided between two straight webs of the housing. Accordingly, the sleeve body of the blocking means 7b, facing each of the two webs of the housing, comprises straight outer faces. The through-opening of the blocking means 7b is larger than the external diameter of the driven member 10 projecting through it. The blocking means 7b is shifted transversally to the forward direction of the driven member 10 against the pressure of a restoring element 7c, which may be designed as a compression spring, by pushing the release means 7a. In the blocked position, the driven member 10 contacts a rear face of the blocking means 7b by a shoulder 29, formed by a thickened section. Transversal displacement of the blocking means 7b releases this stop. The driven member 10 is released from the blocking means 7b, thus allowing advancement in the longitudinal direction subject to the pressure of the drive element 5.

A safety unit ensures that the release means 7a can only be operated, thus releasing the driven member 10, upon a container B having been placed into the housing. The safety unit comprises a release and blocking mechanism 70 and a compression spring 19. The release and blocking mechanism 70 comprises a central sleeve section from which two webs 70a extend forward in the longitudinal direction (section E—E, FIG. 6e). The two webs 70a are projecting through two suitably formed slots in the shoulder 28 of the mixing member 20, contacting the rear edge of the container B. A third web 70b extends in the longitudinal direction toward the rear from the central sleeve section of the release and blocking mechanism 70. This third web 70b projects through the release means 7a, as best seen in the joint longitudinal section and the two sections F—F and G—G (FIGS. 6f and 6g).

At the level of the release means 7a, i.e., in the section through which the release means 7a projects, the third web 70b of the release and blocking mechanism 70 comprises a longitudinal slot. When actuating the release means 7a, a rib 7a of the release means 7a, said rib 7a projecting radially inward, enters into this longitudinal slot if the slot of the release and blocking mechanism 70 being at the same level as the internal rib 7a of the release means 7a. When seen in longitudinal direction, behind the slotted section, the third web 70b is designed as a closed web, i.e., without an opening. A compression spring 19 is provided between the web 9 of the housing and a shoulder extending inward from the internal jacket face of the central sleeve section of the release and blocking mechanism 70. When a container B has been inserted, the frontal webs 70a of the release and blocking mechanism 70 push against the rear edge of the container B, thus being retained in the position shown in the longitudinal section of FIG. 1 in which the internal rib 7a of the release means 7a can enter into the slot of the release and blocking mechanism 70, thus displacing the blocking means 7b transversally. Should no container have been inserted, the release and blocking mechanism 70 is pushed forward by the compression spring 19 into the annular gap, which is then free, until the central sleeve section of the release and blocking mechanism 70 contacts the shoulder 28 of the mixing member 20. In this blocked position of the release and blocking mechanism 70, the rear closed section of the third web 70b is positioned in front of the internal rib 7a of the release means 7a. In this case, transversal shifting of the release means 7a is not possible. The drive unit is therefore blocked.

A drive coupling exists between the driven member 10, projecting through the mixing member 20, and the mixing member 20 with the effect that the mixing member 20 is driven along by the driven member 10 upon advancement of the driven member 10, i.e., being itself shifted in the forward direction in relation to the housing. The coupling is effected by a connection in the frontal section of the mixing member 20, the connection residing in positive and non-positive locking, similar to the coupling of the embodiment of FIG. 1. The mixing member 20 has been allocated a dual function, including that of a transfer member and is therefore designated the mixing and transfer member 20 in the following.

As a variation from the coupling of the embodiment of FIG. 1, the flexible and elastic washer 21 may be accommodated in a groove formed on the internal jacket of the mixing and transfer member 20, and the driven member 10 therefore only comprises a contact pressure surface 17 for the washer 21, said contact pressure surface 17 effecting the driving along of the mixing and transfer member 20. The contact pressure surface 17 forms a first coupling means, with a contact pressure surface 27 formed by the groove of the mixing and transfer member 20 forming a second and the washer 21 a third coupling means.

Within a section arranged in the container B, the mixing and transfer member 20 and the driven member 10 may form a dosing unit. For this purpose, the mixing and transfer member 20 is provided with a recess in an internal jacket section being rearward of the first coupling means 17. This recess comprises two grooves 25 and 26, extending in forward direction, arranged parallel to each other at an offset angle. The grooves 25 and 26 extend in forward direction with different lengths. The shorter groove 25 is formed as a dead groove in the jacket face and the longer groove 26 is limited in the forward direction by the rear web of the accommodation for the third coupling means 21. In relation to forward direction, the rear ends of the grooves 25 and 26 are ending at the same height in a widened section of the recess, as best seen in the longitudinal section of FIG. 6*b*, in combination with sections C—C, D—D and E—E (FIGS. 6*c*, 6*d*, and 6*e*). The widening of the recess ranges to the rear face of the frontal sleeve section of the mixing and transfer member 20. The opposing side walls of the widened section ending there are extended in the forward direction by one each of the two grooves 25 and 26.

The driven member 10 is provided with a radially projecting cam 16. In the initial position of the injection device, the cam 16 engages in the widened section of the recess in the mixing and transfer member 20. The recess, comprising the two grooves 25 and 26, is a first dosing means, and the cam 16 forms a second dosing means of the dosing unit.

In a first dosing position, the cam 16 is located flush with the groove 25 on the first side wall of the widened section, the side wall extending in the forward direction, and in the second dosing position the cam 16 is located flush with the groove 26 on the second side wall of the widened section of the recess, said second side wall extending in the forward direction. In the initial position of the injection device, the driven member 10 is rotatable around its longitudinal axis in either direction between these two dosing positions. The two side walls of the widened section of the recess define the two rotational and dosing positions of the driven member 10, and the lengths of the two narrow grooves 25 and 26 define the volume of the active substance solution being dispensable during one injection.

The widened section of the recess in the mixing and transfer member 20 could also be extended to the end of the short groove 25 in the forward direction, thus providing a simple stepped recess in the forward direction.

For auto-injection, the auto-injection device is placed with its needle safety sleeve 50' on the surface of the tissue, in particular the human skin, the needle safety sleeve 50' being retractable in relation to the frontal housing, i.e, the frontal needle protection 1. The needle safety sleeve 50' is pushed back to its most rear position in relation to the housing by pressure being applied against the surface of the tissue. The injection needle N, firmly attached to the outlet of the container B pointing in the forward direction, is initially covered beyond its front tip by the needle protection 1 and the needle safety sleeve 50' covering the same, thus not touching the tissue surface.

After having positioned the driven member 10 into the required rotational and dosing position by means of the metering sleeve D, the user pushes the release means 7*a*, which may be a tab, inward in the radial direction for actuating, i.e., inserting the needle and dispensing the active substance solution. When pushing the release means 7*a* inwards, the blocking means 7*b*, which may be a stop, is pushed away from underneath the stop shoulder 29, thus releasing the driven member 10. The driven member 10 is shifted forward in relation to the housing subject to the pressure of the drive element 5. By means of the coupling the mixing and transfer member 20 is also shifted forward. The positive and non-positive locking between the driven member 10 and the mixing and transfer member 20 is sufficiently strong for the mixing and transfer member 20 to be driven along, which in turn, by applying pressure by its shoulder 28 against the container holder 30 and the container B, advances these in relation to the housing and against the restoring force of the restoring element 33 up to a frontal position, defined by a stop 31 a formed on the housing.

In the frontal position of the container holder 30 and the container B, the coupling releases the drive connection between the driven member 10 and the mixing and transfer member 20. Subject to continued pressure of the drive element 5 and due to the fixing of the mixing and transfer member 20, the flexible washer 21 is compressed and pushed over the chamfered shoulder 17. The driven member 10 now advances further, also in relation to the mixing and transfer member 20, simultaneously pushing the two pistons K1 and K2 forward in the container toward the container outlet. The active substance solution is dispensed through the needle N, inserted into the tissue in the frontal position of the container.

In the first dosing position, the advance movement of the driven member 10 is limited by the frontal end of the groove 25. In the first dosing position, dispensing ends upon the cam 16 touching that wall of the groove 25 which extends in circumferential direction.

After retraction of the needle N, the injection device is prepared for a second injection, with only the driven member 10 initially being retracted against forward direction in relation to the mixing and transfer member 20. The driven member 10 is provided with a plunger 11 at its frontal end, having the shape of a flange-type widened section. When dispensing the active substance solution, the driven member 10 pushes with its plunger 11 against the rear piston K2 and upon retracting, the rear circumferential shoulder face of the plunger 11, pushes against the web projecting from the internal jacket face of the mixing and transfer member 20, forming the front wall of the groove accommodating the third coupling means 21. When retracted further, the driven member 10 takes along with it the mixing and transfer member 20, i.e. up to its rear position, as shown in FIG. 1. The container holder 30 and the container B located therein, follow the movement of the mixing and transfer member 20 subject to the pressure of the restoring element 33. The restoring force of the restoring element 33 may be low as compared to the drive force of the drive element 5, therefore not interfering upon pushing the container B forward for inserting the needle N.

For the next injection, the driven member 10 is rotated into its second dosing position in which the cam 16 is positioned flush with the groove 26. In this position, the driven member 10 can be advanced in relation to the mixing and transfer member 20 so that the residual active substance solution in the container is dispensed upon the drive unit being actuated, i.e., by actuating the release means 7. Forward movement is limited by a circumferential web forming the rear wall of the accommodating groove for the third coupling means 21.

In the foregoing description, embodiments of the invention have been presented for the purpose of illustration and description. They are not intended to be exhaustive or to limit the invention to the precise form disclosed. Modifications or variations are possible in light of the above teachings, and the described embodiments were chosen and described to provide an illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. An auto-injection device for administering a product, comprising:
   a) a housing;
   b) a container having an outlet and carrying a needle at said outlet, the container being shiftably accommodated by the housing; and
   c) a driven member of a drive unit operably coupled to the housing, the driven member being shiftably accommadated by the housing wherein, during an auto-injection, the driven member advances the container to a predetermined frontal position in relation to the housing, and advances a piston within the container for dispensing of the product, wherein the driven member remains uncoupled with the piston, and coupled with the container until the container reaches the predetermined frontal position, and upon the container reaching the predetermined frontal position, the driven member becomes decoupled from the container and becomes coupled with the piston for advancement of the piston within the container.

2. The device of claim 1, further comprising:
   a transfer member which is driven by the driven member, the transfer member being adapted to push the container in a forward direction when advancing; and
   a coupling which affects the driving motion between the driven member and the transfer member, wherein when the container reaches its predetermined frontal position, and the driven member advances further, the driven member advances the piston while pushing against it within the container.

3. The device of claim 2, wherein the coupling between the driven member and the transfer member comprises a first coupling means connected to the driven member and a second coupling means connected to the transfer member, the second coupling means being in engagement with the first coupling means, thus causing the driving motion of the transfer member, the engagement being released by a relative rotation caused by a joint advance movement between the driven member and the transfer member around a rotational axis pointing in a forward direction.

4. The device of claim 3, wherein the joint advance movement is converted into the relative rotation by a coulisse guiding formed between the driven member and the housing, and wherein the transfer member and the coulisse guiding secure against rotation and displacement.

5. The device of claim 3, wherein the joint advance movement is converted into the relative rotation by a coulisse guiding formed between the transfer member and the housing, and wherein the driven member and the coulisse guiding secure against rotation and displacement.

6. The device of claim 1, wherein the coupling between the driven member and the container comprises a positive locking connection.

7. The device of claim 1, wherein the coupling between the driven member and the container comprises a non-positive locking connection of the driven member and a transfer member.

8. The device of claim 7, wherein the coupling between the driven member and the container comprises a first coupling means connected to the driven member and a second coupling means connected to the transfer member, the second coupling means being in engagement by means of a third coupling means with the transfer member, thus causing the transfer member to be driven forward, wherein at least one of the coupling means is flexible and yields under the influence of a force exerted at the end of the forward movement of the container, thus causing disengagement.

9. The device of claim 8, wherein said third coupling means is a flexible ring, transmitting a forward pressure of said first coupling means to said second coupling means and being shifted beyond said first coupling means or said second coupling means when a predetermined maximum force acting in the forward direction is exceeded.

10. The device of claim 1, further comprising a damper between a transfer member and the driven member for compensation of a decrease of a drive force effecting the advancement of the driven member.

11. The device of claim 1, wherein the container is formed by a multi-chamber ampoule having a rear piston and a frontal piston, and a mixing member containing a mixing tube for advancing the rear piston towards the frontal piston, the mixing tube being a transfer member.

12. The device of claim 11, wherein said transfer member comprises a dosing means, which by interacting with the drive unit allows for the selection of a product dose which is to be administered.

13. The device of claim 1, further comprising a needle safety sleeve shiftably arranged on said housing and being blocked in a frontal position surrounding said needle against rearward shifting relative to said housing when said needle is in an advanced position.

14. The device of claim 13, further comprising a container holder being shiftably accommodated by said housing and being advanced together with said container, effecting a blocking of said needle safety sleeve when said container is in its frontal position.

15. An injection device comprising a housing, a container shiftably accommodated by the housing, the container carrying a needle and accommodating a moveable piston, and a drive unit comprising a driven member shiftably accommodated by the housing wherein, during an injection, the driven member is coupled to the container, and advances the container to a predetermined position in relation to the housing, wherein, upon reaching the predetermined position, the driven member is decoupled from the container and coupled with the piston for moving the piston within the container.

16. An auto-injection device for administering a product, comprising:

a) a housing;

b) a container having an outlet and carrying a needle at said outlet, the container being shiftably accommodated by the housing; and c) a driven member of a drive unit, the driven member being shiftably accommodated by the housing wherein, during an auto-injection, the driven member advances the container to a predetermined frontal position in relation to the housing and advances a piston within the container for dispensing of the product, wherein d) the driven member is not coupled with the piston and is coupled with the container until the container reaches the predetermined frontal position, and upon the container reaching the predetermined frontal position, the driven member is decoupled from the container and coupled with the piston from advancing the piston within the container.

* * * * *